US010553314B2

(12) United States Patent
Ikeda et al.

(10) Patent No.: US 10,553,314 B2
(45) Date of Patent: Feb. 4, 2020

(54) BIOLOGICAL CLOCK TIME CALCULATING APPARATUS AND BIOLOGICAL CLOCK TIME CALCULATING METHOD

(71) Applicant: SEIKO EPSON CORPORATION, Tokyo (JP)

(72) Inventors: Akira Ikeda, Chino (JP); Sakiko Shimizu, Matsumoto (JP); Ayae Sawado, Kai (JP); Hiroyuki Masuda, Chino (JP)

(73) Assignee: SEIKO EPSON CORPORATION, Tokyo (JP)

( * ) Notice: Subject to any disclaimer, the term of this patent is extended or adjusted under 35 U.S.C. 154(b) by 189 days.

(21) Appl. No.: 15/662,839

(22) Filed: Jul. 28, 2017

(65) Prior Publication Data
US 2018/0039749 A1 Feb. 8, 2018

(30) Foreign Application Priority Data

Aug. 8, 2016 (JP) .................................. 2016-155842

(51) Int. Cl.
*A61B 5/00* (2006.01)
*G16H 40/63* (2018.01)
*G06F 19/00* (2018.01)

(52) U.S. Cl.
CPC .......... *G16H 40/63* (2018.01); *G06F 19/3481* (2013.01)

(58) Field of Classification Search
USPC ................................................. 600/300–301
See application file for complete search history.

(56) References Cited

U.S. PATENT DOCUMENTS

| 6,519,142 | B1 * | 2/2003 | Lai ......................... G06F 1/1626 345/156 |
| 6,619,836 | B1 * | 9/2003 | Silvant ................... G04G 17/08 368/281 |
| 7,027,621 | B1 * | 4/2006 | Prokoski ............ G06K 9/00248 180/272 |
| 7,608,041 | B2 * | 10/2009 | Sutton ................... A61M 21/00 600/300 |
| 7,618,260 | B2 * | 11/2009 | Daniel ................. A44C 5/0007 24/311 |
| 7,764,996 | B2 * | 7/2010 | Zhang ................ A61B 5/02055 607/3 |

(Continued)

FOREIGN PATENT DOCUMENTS

| JP | H05-3878 A | 1/1993 |
| JP | 2010-158267 A | 7/2010 |

(Continued)

*Primary Examiner* — Michael W Kahelin
*Assistant Examiner* — Shirley X Jian
(74) *Attorney, Agent, or Firm* — Oliff PLC

(57) ABSTRACT

A biological clock time calculating apparatus includes: a measuring portion which measures bio-information that changes on a daily basis; and an arithmetic processing portion which calculates biological clock time based on a measurement result of the measuring portion. A biological clock time calculating method may be configured to include: measuring bio-information which changes on a daily basis; and calculating biological clock time based on the measurement result.

11 Claims, 11 Drawing Sheets

(56) References Cited

U.S. PATENT DOCUMENTS

| | | | | |
|---|---|---|---|---|
| 7,783,353 B2* | 8/2010 | Libbus | A61N 1/36117 | 607/18 |
| 8,005,540 B2* | 8/2011 | Zhang | A61B 5/02055 | 607/3 |
| 8,140,143 B2* | 3/2012 | Picard | A61B 5/0531 | 600/388 |
| 8,142,357 B2* | 3/2012 | Suyama | A61B 5/02055 | 368/11 |
| 8,157,730 B2* | 4/2012 | LeBoeuf | G16H 50/30 | 600/300 |
| 8,401,636 B2* | 3/2013 | Zhang | A61B 5/02055 | 607/3 |
| 8,484,153 B2* | 7/2013 | Mott | A61B 5/4857 | 706/52 |
| 8,764,654 B2* | 7/2014 | Chmiel | G06F 13/4239 | 600/301 |
| 8,805,493 B2* | 8/2014 | Zhang | A61B 5/02055 | 607/3 |
| 9,163,983 B2* | 10/2015 | Olds | A61N 5/0618 | |
| 9,189,739 B2* | 11/2015 | Mott | A61B 5/4857 | |
| 9,223,935 B2* | 12/2015 | Heneghan | G06F 19/3418 | |
| 9,542,531 B2* | 1/2017 | Chmiel | G06F 13/4239 | |
| 9,579,521 B2* | 2/2017 | Ferraz Rigo | A61N 5/0618 | |
| 9,594,354 B1* | 3/2017 | Kahn | G04G 21/00 | |
| 9,636,520 B2* | 5/2017 | Pedersen | A61N 5/0618 | |
| 9,802,060 B2* | 10/2017 | Olds | A61N 5/0618 | |
| 10,076,286 B1* | 9/2018 | Bajaj | A61B 5/7275 | |
| 10,179,064 B2* | 1/2019 | Connor | A61F 7/0097 | |
| 10,261,475 B1* | 4/2019 | Kahn | G04G 21/00 | |
| 10,368,811 B1* | 8/2019 | Bajaj | A61B 5/6802 | |
| 2002/0005784 A1* | 1/2002 | Balkin | A61B 5/16 | 340/573.1 |
| 2002/0101457 A1* | 8/2002 | Lang | G06F 1/163 | 715/856 |
| 2004/0235424 A1* | 11/2004 | Kim | H04M 1/72533 | 455/68 |
| 2005/0015122 A1* | 1/2005 | Mott | A61M 21/00 | 607/88 |
| 2006/0106437 A1* | 5/2006 | Czeisler | A61M 21/02 | 607/88 |
| 2006/0200008 A1* | 9/2006 | Moore-Ede | B60K 28/06 | 600/300 |
| 2007/0279852 A1* | 12/2007 | Daniel | A44C 5/0007 | 361/679.03 |
| 2008/0114219 A1* | 5/2008 | Zhang | A61B 5/02055 | 600/301 |
| 2008/0162182 A1* | 7/2008 | Cazares | G06Q 50/22 | 705/2 |
| 2009/0131767 A1* | 5/2009 | Arne | A61B 5/6862 | 600/302 |
| 2010/0121158 A1* | 5/2010 | Quevedo | A61B 5/0482 | 600/301 |
| 2010/0138379 A1* | 6/2010 | Mott | A61B 5/4857 | 706/52 |
| 2010/0174153 A1* | 7/2010 | Nakagawa | G16H 40/63 | 600/301 |
| 2010/0280564 A1* | 11/2010 | Zhang | A61B 5/02055 | 607/3 |
| 2011/0015495 A1* | 1/2011 | Dothie | G16H 10/60 | 600/300 |
| 2011/0144528 A1* | 6/2011 | Gurley | A61B 5/01 | 600/549 |
| 2011/0301530 A1* | 12/2011 | Zhang | A61B 5/02055 | 604/20 |
| 2012/0296400 A1* | 11/2012 | Bierman | A61M 21/00 | 607/88 |
| 2013/0218030 A1* | 8/2013 | Barroso | A61B 5/4857 | 600/483 |
| 2013/0226078 A1* | 8/2013 | Zhang | A61B 5/02055 | 604/66 |
| 2013/0260800 A1* | 10/2013 | Asakawa | H04W 4/02 | 455/457 |
| 2013/0282646 A1* | 10/2013 | Mott | A61B 5/4857 | 706/52 |
| 2013/0289419 A1* | 10/2013 | Berezhnyy | A61B 5/02055 | 600/484 |
| 2013/0289476 A1* | 10/2013 | Zhang | A61B 5/02055 | 604/66 |
| 2013/0301034 A1* | 11/2013 | Olds | A61N 5/0618 | 356/51 |
| 2014/0276244 A1* | 9/2014 | Kamyar | A61B 5/1112 | 600/595 |
| 2015/0157220 A1* | 6/2015 | Fish | A61B 5/02055 | 600/301 |
| 2015/0186594 A1* | 7/2015 | Zhang | A61N 5/0618 | 703/2 |
| 2015/0300875 A1* | 10/2015 | Maass | A61B 5/681 | 250/208.2 |
| 2015/0320588 A1* | 11/2015 | Connor | A61F 7/0097 | 607/107 |
| 2016/0016005 A1* | 1/2016 | Olds | A61N 5/0618 | 356/215 |
| 2016/0123802 A1* | 5/2016 | Likovich | G01J 1/0271 | 356/221 |
| 2016/0199000 A1* | 7/2016 | Gimenez | G01J 1/0271 | 315/151 |
| 2016/0270718 A1* | 9/2016 | Heneghan | A61B 5/0533 | |
| 2017/0007178 A1* | 1/2017 | Aubert | A61B 5/1118 | |
| 2018/0345014 A1* | 12/2018 | Gozani | A61N 1/0476 | |

FOREIGN PATENT DOCUMENTS

| | | |
|---|---|---|
| JP | 2013-208315 A | 10/2013 |
| JP | 2014-168492 A | 9/2014 |
| WO | 2014/133146 A1 | 9/2014 |

* cited by examiner

372

| BODY PROFILE | | MEASUREMENT PART | CHARACTERISTICS PERIOD REFERENCE EXPRESSION TIME $\tau_0$ |
|---|---|---|---|
| GENDER | AGE | | |
| MALE | YOUNGER THAN 10 YEARS OLD | WRIST | XXXX |
| | | CHEST | XXXX |
| | | ⋮ | ⋮ |
| | 10 YEARS OLD OR OLDER AND YOUNGER THAN 20 YEARS OLD | WRIST | XXXX |
| | | ⋮ | ⋮ |
| | 20 YEARS OLD OR OLDER AND YOUNGER THAN 30 YEARS OLD | WRIST | XXXX |
| | | ⋮ | ⋮ |
| | 30 YEARS OLD OR OLDER AND YOUNGER THAN 40 YEARS OLD | WRIST | XXXX |
| | | ⋮ | ⋮ |
| | ⋮ | ⋮ | ⋮ |
| FEMALE | YOUNGER THAN 10 YEARS OLD | WRIST | XXXX |
| | | ⋮ | ⋮ |
| | 10 YEARS OLD OR OLDER AND YOUNGER THAN 20 YEARS OLD | WRIST | XXXX |
| | | ⋮ | ⋮ |
| | ⋮ | ⋮ | ⋮ |

| AREA INFORMATION | | | SEASON | DURATION OF SUNSHINE | CORRECTED VALUE |
|---|---|---|---|---|---|
| NAME OF COUNTRY | NAME OF REGION | POSITIONAL INFORMATION | | | |
| XX | XXX | XXXXXX | MARCH TO MAY (SPRING) | XXXX | XXXXX |
| | | | JUNE TO AUGUST (SUMMER) | XXXX | XXXXX |
| | | | SEPTEMBER TO NOVEMBER (AUTUMN) | XXXX | XXXXX |
| | | | DECEMBER TO FEBRUARY (WINTER) | XXXX | XXXXX |
| | XXX | XXXXXX | MARCH TO MAY (SPRING) | XXXX | XXXXX |
| | | ⋮ | ⋮ | ⋮ | ⋮ |
| | ⋮ | ⋮ | ⋮ | ⋮ | ⋮ |
| XX | XXX | XXXXXX | MARCH TO MAY (SPRING) | XXXX | XXXXX |
| | | ⋮ | ⋮ | ⋮ | ⋮ |
| | ⋮ | ⋮ | ⋮ | ⋮ | ⋮ |
| ⋮ | ⋮ | ⋮ | ⋮ | ⋮ | ⋮ |

| TYPE OF ACTIVITY OF DAILY LIFE | INFORMING AND HOME ELECTRONIC APPLIANCE CONTROL TIMING (BIOLOGICAL CLOCK TIME) | INFORMING CONTENTS | CONTROL SIGNAL |
|---|---|---|---|
| WAKING UP | T300 | XXXXXXX | XXXXXXXX |
| EATING BREAKFAST | T301 | XXXXXXX | XXXXXXXX |
| ⋮ | ⋮ | ⋮ | ⋮ |
| BATHING | T321 | XXXXXXX | XXXXXXXX |
| ⋮ | ⋮ | ⋮ | ⋮ |
| GOING TO BED | T331 | XXXXXXX | XXXXXXXX |
| ⋮ | ⋮ | ⋮ | ⋮ |

TIMING TABLE (FOR BIOLOGICAL CLOCK TIME)

FIG.11

BIOLOGICAL CLOCK TIME CALCULATING APPARATUS AND BIOLOGICAL CLOCK TIME CALCULATING METHOD

BACKGROUND

Technical Field

The present invention relates to a biological clock time calculating apparatus and a biological clock time calculating method for calculating biological clock time.

In recent years, an experiment for successively measuring bio-information, such as a body temperature, a blood pressure, and a quantity of physical activities, and for using the bio-information in health management or the like, has become flourished. It is known that the bio-information varies in a predetermined period, for example, on a daily, monthly, or yearly basis. It is known that such periodic variation of the bio-information appears in accordance with a biorhythm, and from the related art, various technologies for grasping the biorhythm, which, for example, measure and display the biorhythm, or evaluate the biorhythm are disclosed (for example, refer to JP-A-2010-158267, JP-A-2014-168492, and JP-A-5-3878). The biorhythm is mainly adjusted by a biological clock (which is also called a biological clock), and has a close relationship with an activity situation or health state of a living body, and thus, grasping the biorhythm has an important meaning in health management or the like.

However, in the technologies of the related art, such as JP-A-2010-158267, JP-A-2014-168492, and JP-A-5-3878, even when the biorhythm can be grasped, it is not possible to know the time of the biological clock in which the biorhythm is made.

SUMMARY

An advantage of some aspects of the invention is to provide a technology for calculating the biological clock time in which a biorhythm is made on a daily basis.

A first aspect of the invention is directed to a biological clock time calculating apparatus including: a measuring portion which measures bio-information that changes on a daily basis; and an arithmetic processing portion which calculates biological clock time based on a measurement result of the measuring portion.

As a second aspect of the invention, the invention may be configured as a biological clock time calculating apparatus including: an input portion which inputs a measurement result of a measuring portion that measures bio-information that changes on a daily basis; and an arithmetic processing portion which calculates biological clock time based on the measurement result.

As another aspect of the invention, the invention may be configured as a biological clock time calculating method including: measuring bio-information which changes on a daily basis; and calculating biological clock time based on the measurement result.

According to the first aspect or the like of the invention, it is possible to measure the bio-information which changes on a daily basis, or to calculate the biological clock time from a periodic change in the bio-information on a daily basis by inputting and using the measurement result.

As a third aspect of the invention, the biological clock time calculating apparatus according to the first or second aspect of the invention may be configured such that the arithmetic processing portion sets a reference expression time which is a reference time at which a characteristics period of the bio-information is expressed, and calculates the biological clock time based on a time difference between an expression time of the characteristics period determined from a time series change of the bio-information measured by the measuring portion, and the reference expression time.

According to the biological clock time calculating apparatus according to the third aspect of the invention, it is possible to calculate the biological clock time from the time difference between the reference expression time according to the characteristics period of the bio-information and the expression time of the characteristics period obtained from the measurement result of the bio-information.

As a fourth aspect of the invention, the biological clock time calculating apparatus according to the third aspect of the invention may be configured such that the arithmetic processing portion sets the reference expression time based on any of a body profile of a target person to be measured, a residential area of the target person to be measured, and a season in the residential area.

According to the biological clock time calculating apparatus according to the fourth aspect of the invention, it is possible to calculate the biological clock time by using the reference expression time which corresponds to any of the body profile of the target person to be measured, the residential area of the target person to be measured, and the season in the residential area.

As a fifth aspect of the invention, the biological clock time calculating apparatus according to any of the first to fourth aspects of the invention may be configured such that the arithmetic processing portion performs first informing processing of informing any of the biological clock time and a time difference between the biological clock time and a current time.

According to the biological clock time calculating apparatus according to the fifth aspect of the invention, it is possible to inform the biological clock time, or to inform the time difference between the biological clock time and the current time.

As a sixth aspect of the invention, the biological clock time calculating apparatus according to any of the first to fifth aspects of the invention may be configured such that the arithmetic processing portion performs second informing processing related to a biorhythm of the target person to be measured by using the biological clock time.

According to the biological clock time calculating apparatus according to the sixth aspect of the invention, it is possible to perform the informing related to the biorhythm of the target person to be measured.

As a seventh aspect of the invention, the biological clock time calculating apparatus according to any of the first to sixth aspects of the invention may be configured such that the arithmetic processing portion performs third informing processing in a case where the time difference between the biological clock time and the current time satisfies a predetermined threshold value condition.

According to the biological clock time calculating apparatus according to the seventh aspect of the invention, it is possible to perform the informing which corresponds to the time difference between the biological clock time and the current time.

As an eighth aspect of the invention, the biological clock time calculating apparatus according to any of the first to seventh aspects of the invention may be configured such that the arithmetic processing portion performs first external device control processing of sending a given control signal based on the biological clock time, to any of a home electronic appliance and an external electronic device.

According to the biological clock time calculating apparatus according to the eighth aspect of the invention, it is possible to control any of the home electronic appliance and the external electronic device, based on the biological clock time.

As a ninth aspect of the invention, the biological clock time calculating apparatus according to any of the first to eighth aspects of the invention may be configured such that the arithmetic processing portion performs second external device control processing of sending a given control signal to any of a home electronic appliance and an external electronic device, in a case where the time difference between the biological clock time and the current time satisfies a predetermined threshold value condition.

According to the biological clock time calculating apparatus according to the ninth aspect of the invention, it is possible to control any of the home electronic appliance and the external electronic device, in accordance with the time difference between the biological clock time and the current time.

As a tenth aspect of the invention, the biological clock time calculating apparatus according to any of the first to ninth aspects of the invention may be configured such that the bio-information includes any one of a body temperature, a blood pressure, arterial oxygen saturation, and a pulse rate.

According to the biological clock time calculating apparatus according to the tenth aspect of the invention, it is possible to calculate the biological clock time by using any one of the body temperature, the blood pressure, the arterial oxygen saturation, and the pulse rate.

As an eleventh aspect of the invention, the biological clock time calculating apparatus according to any of the first to tenth aspects of the invention may be configured such that the measuring portion measures plural types of bio-information, and the arithmetic processing portion estimates specific bio-information from the measurement result of the plural types of bio-information, and calculates the biological clock time based on the specific bio-information.

According to the biological clock time calculating apparatus according to the eleventh aspect of the invention, it is possible to calculate the biological clock time by estimating and using the specific bio-information from the plural types of bio-information.

As a twelfth aspect, in the biological clock time calculating apparatus according to any of the first to eleventh aspects of the invention may be configured such that the biological clock time calculating apparatus further includes a first needle which indicates the current time; a second needle which indicates the biological clock time; and a needle handling control portion which performs a needle handling control of the first needle and the second needle.

According to the biological clock time calculating apparatus according to the twelfth aspect of the invention, it is possible to display the biological clock time together with the current time by the first needle which indicates the current time and the second needle which indicates the biological clock time.

BRIEF DESCRIPTION OF THE DRAWINGS

The invention will be described with reference to the accompanying drawings, wherein like numbers reference like elements.

FIG. 9 is a view illustrating a data configuration example of a reference expression time table.

FIG. 10 is a view illustrating a data configuration example of a reference expression time correction table.

FIG. 11 is a view illustrating a data configuration example of a timing table for biological clock time.

DESCRIPTION OF EXEMPLARY EMBODIMENTS

Figure 1:
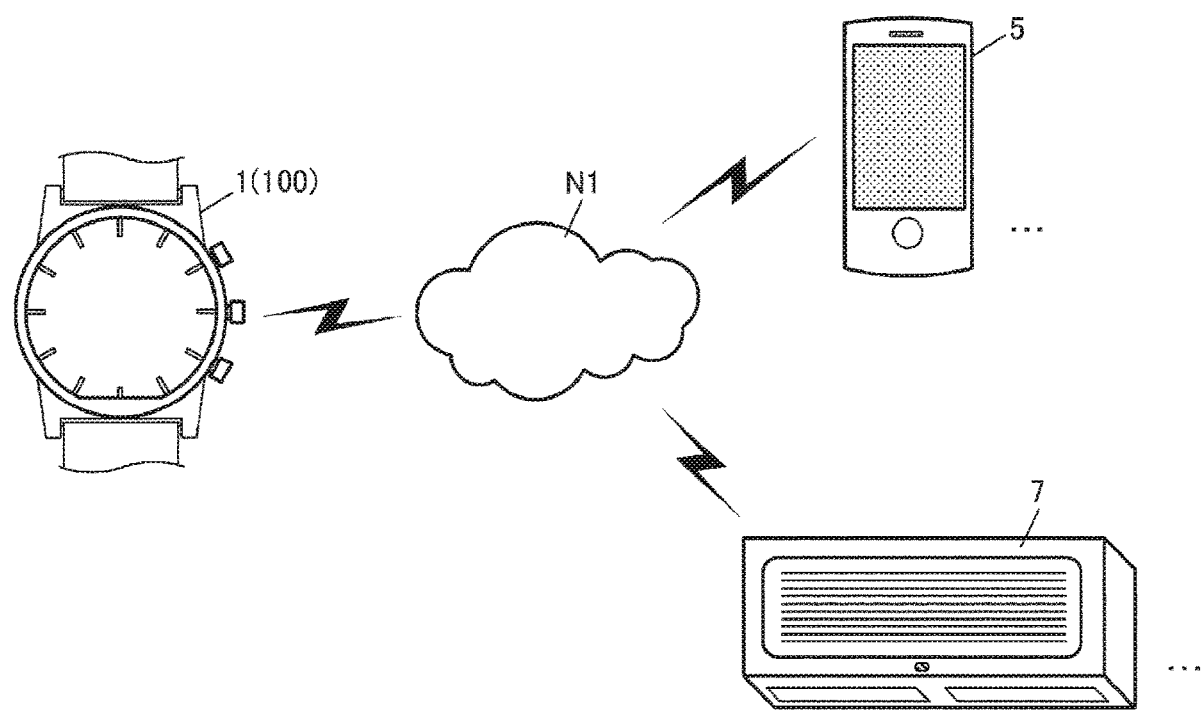
FIG. 1 is a schematic view illustrating a configuration example of the entire system provided with an electronic device.

Hereinafter, appropriate embodiments of the invention will be described with reference to the drawings. In addition, the invention is not limited to the embodiments which will be described hereinafter, and the aspects that can employ the invention are not limited to the following embodiments. In addition, in the description of the drawings, the same part will be given the same reference numerals.

FIG. 1 is a schematic view illustrating a configuration example of the entire system provided with an electronic device 1 which is a biological clock time calculating apparatus 100 of the embodiment. The electronic device 1 of the embodiment is configured such that data communication is possible between the electronic device 1 and an external electronic device 5 or a home electronic appliance 7 via a predetermined communication line N1. The external electronic device 5 is, for example, a smartphone, a mobile phone, a personal computer, a tablet type computer, or a game device. In addition, the home electronic appliance 7 is, for example, air conditioning equipment, alighting device, alight controlling device, an acoustic device, a video device, or a perfume forming device (aroma diffuser). The light controlling device includes an electric curtain or a shutter. The lighting device may be provided with a light controlling function.

Figure 2:
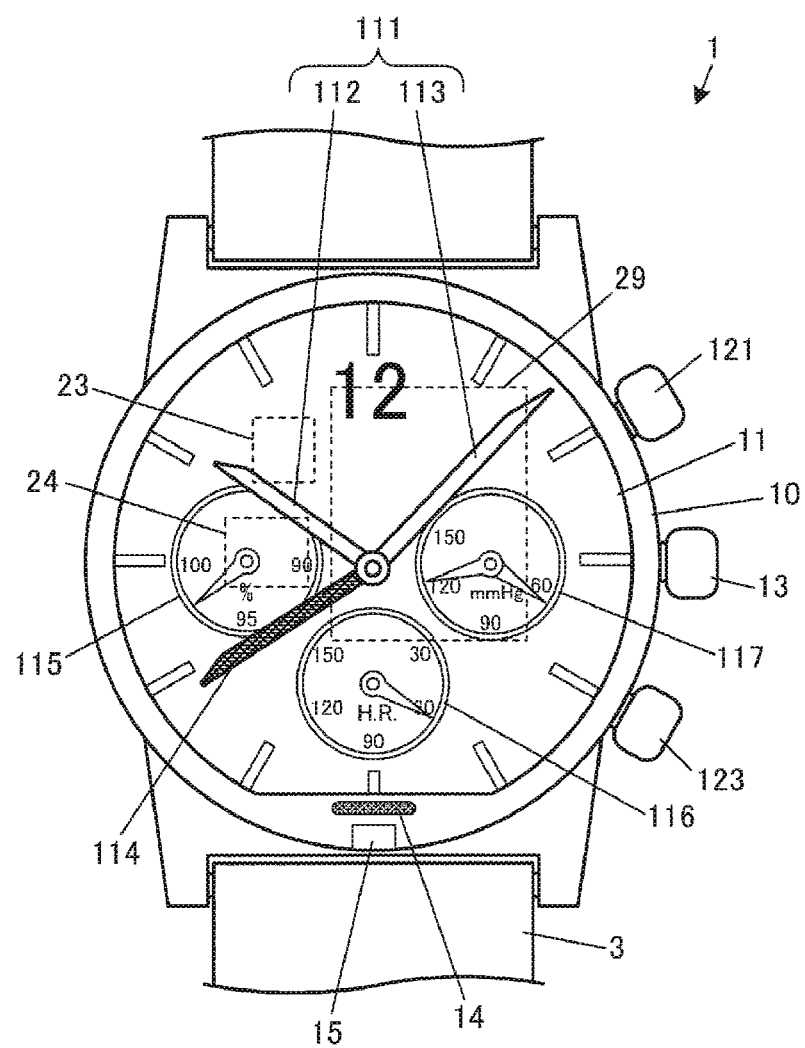
FIG. 2 is an appearance view when a biological clock time calculating apparatus is viewed from a front surface side.
Figure 3:
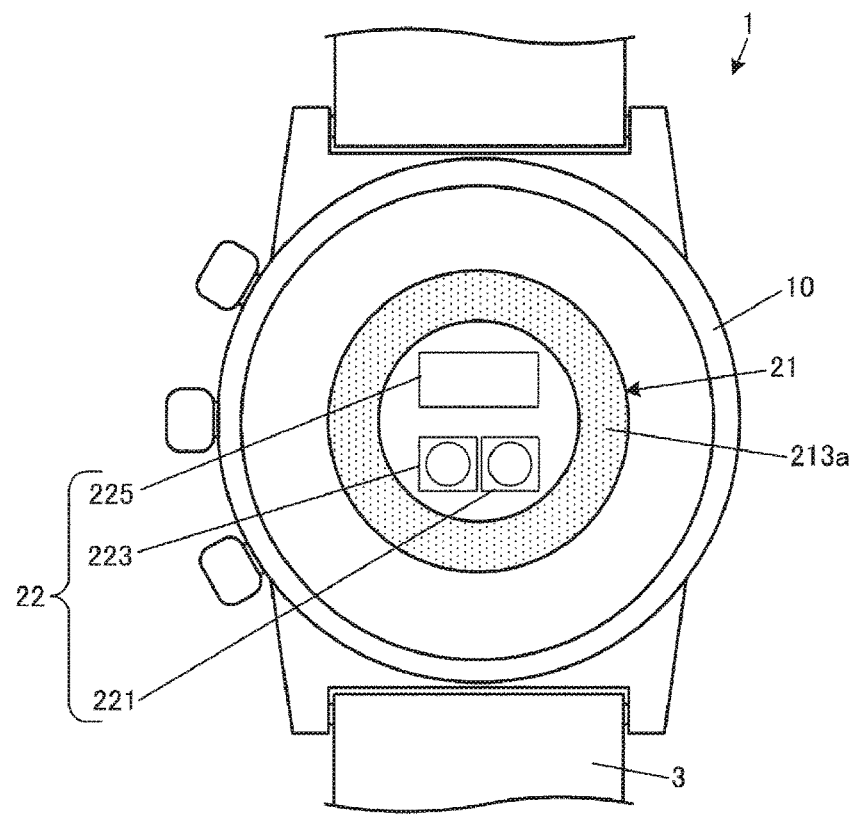
FIG. 3 is an appearance view when the biological clock time calculating apparatus is viewed from a rear surface side.

FIGS. 2 and 3 are appearance views illustrating a configuration example of the electronic device 1, FIG. 2 illustrates a front surface (a surface which is oriented outward when being installed on a user who is a target person to be measured) thereof, and FIG. 3 illustrates a rear surface (a surface which is in contact with the skin of the user when being installed on the user). The electronic device 1 of the embodiment is a wristwatch which displays a current biological clock time together with a current time, and is installed and fixed to a biological surface (skin surface of the wrist) by winding a band 3 provided in a main body case 10 around the wrist of the user.

In addition, the configuration is not limited to a configuration of being wound around the skin surface by the band 3, and a configuration of adhering and installing to the skin surface of the user by using an adhesive sheet or gel which is attachable to and detachable from the skin surface may be employed. In addition, a measurement part on which the electronic device 1 is installed is not limited to the wrist. For example, forehead, neck, upper arm, ankle, chest, trunk, or back of a hand or foot, may be appropriately selected as the measurement part.

The electronic device 1 includes a character plate 11 for analog-displaying the current time and the biological clock time, on the inside of the main body case 10. In addition, in an outer circumferential portion of the main body case 10, operation switches 121 and 123 for inputting various operations, such as a measurement start or a measurement stop of bio-information, a crown 13 for manually adjusting the current time, a speaker 14, and a light emitting diode (LED) 15, and the like are installed.

The character plate 11 includes a first needle 111 which indicates the current time, and a second needle 114 which indicates the biological clock time, on the front surface thereof. The first needle 111 is illustrated as two needles configured of an hour hand 112 and a minute hand 113, but may be three needles including a second hand. The second needle 114 is only the hour hand in the embodiment, but may be two needles including the minute hand. Each of the needles 111 and 114 is driven and handled by a movement which is not illustrated and is provided on a rear surface side of the character plate 11.

In addition, on the front surface of the character plate 11, three display meters (in-dials) 115, 116, and 117 which respectively display a blood pressure, arterial oxygen saturation (SpO2), and a pulse rate (heart rate) which are measured as the bio-information are installed. One of two needles of the display meter 117 which displays the blood pressure indicates a diastolic blood pressure (lowest blood pressure) and the other one indicates a systolic arterial pressure (highest blood pressure).

In addition, each of the displays, such as the current time, the biological clock time, and the bio-information, by the character plate 11 is not limited to the analog display that uses the needles 111 and 114 or the display meters 115 to 117. For example, each of the displays may be performed by using the display device, such as a touch panel, instead of the character plate 11. At this time, the time display is not limited to the analog display and may be a digital display. In addition, the time display may be performed by 7 segment displays that use the LED.

The electronic device 1 includes a plurality of sensors that are appropriately disposed. For example, the electronic device 1 has a heat flow sensor 21, an optical sensor 22, a motion sensor 23, and a GPS sensor 24, embedded therein.

The heat flow sensor 21 measures a heat flow generated on the biological surface based on a temperature difference generated on the inside of the heat flow sensor 21, by a heat transmission between the biological surface and an external environment of the measurement part (in the embodiment, wrist) at which the electronic device 1 is installed. For example, an outer shape of the heat flow sensor 21 is a substantially circular shape, and a protective layer 213a that forms one end surface is installed to be exposed on a rear surface of the main body case 10.

Figure 4:
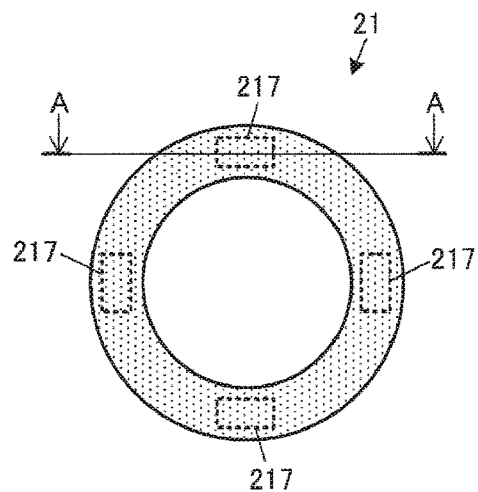
FIG. 4 is a plan view of a heat flow sensor.
Figure 5:
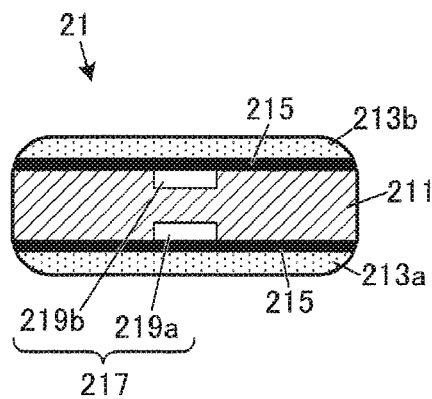
FIG. 5 is a schematic view of a section taken along the line A-A illustrated in FIG. 4.

FIG. 4 is a plan view of the heat flow sensor 21, and FIG. 5 is a schematic view of a section taken along the line A-A illustrated in FIG. 4. In addition, wiring or the like is not illustrated and omitted. As illustrated in FIGS. 4 and 5, the heat flow sensor 21 includes a layered structure in which a heat transmission layer 211, the protective layer 213a that covers a lower side in FIG. 5, and a protective layer 213b that covers an upper side adhere to each other via a heat diffusion layer 215, and is configured such that a plurality (four in FIG. 4) of measuring devices 217 are incorporated on the inside of the heat transmission layer 211.

The measuring device 217 includes a temperature measuring element 219a disposed to be in contact with the protective layer 213a that is on a biological surface side when being installed, and a temperature measuring element 219b disposed to be in contact with the protective layer 213b that is on an external environment side at a position which opposes the temperature measuring element 219a, and outputs a measured temperature of the temperature measuring element 219a as a skin temperature and a measured temperature of the temperature measuring element 219b as a heat transmission temperature. It is possible to measure a heat flux (heat flow per unit area) at the position of the corresponding measuring device 217 from a temperature difference (upper and lower temperature differences) of the measured temperatures by each of the temperature measuring elements 219a and 219b. As the temperature measuring elements 219a and 219b, it is possible to use a thermistor or a thermocouple, for example. In addition, the configuration of the heat flow sensor 21 is not limited to the configuration in which two temperature measuring elements are used, and a known configuration, such as a configuration in which a thermopile is used, can be appropriately selected and used.

The optical sensor 22 includes two light generating portions 221 and 223 which are installed such that a light generating surface thereof is exposed on the rear surface of the main body case 10, and a light receiving portion 225 which is installed such that a light receiving surface thereof is exposed on the rear surface of the main body case 10, at a part on the circular inner side of the heat flow sensor 21. The light generating surface of the light generating portions 221 and 223 and the light receiving surface of the light receiving portion 225 are protected by a transparent cover glass or the like which covers the part on the circular inner side of the heat flow sensor 21.

The light generating portions 221 and 223 can be realized by using a light source, such as an LED or an organic light emitting diode (OLED) which emits irradiation light within a predetermined wavelength region, or a semiconductor layer. The wavelength region of the irradiation light can be appropriately selected in accordance with the target to be measured. In the embodiment, for example, the one light generating portion 221 emits visible light having a first wavelength that is close to the wavelength region of 660 [nm], and the other light generating portion 223 emits near infrared light having a second wavelength that is included in the wavelength region of 880 [nm] to 940 [nm].

The light receiving portion 225 receives transmitted light or reflected light of the irradiation light, and outputs a signal that corresponds to a light receiving amount. For example, the light receiving portion 225 can be realized by a photodiode, a charge coupled device (CCD), or a complementary metal oxide semiconductor (CMOS).

In the optical sensor 22, the irradiation light is emitted from any one or both of the light generating portions 221 and 223, arithmetic processing is performed with respect to the light receiving result (output value of the light receiving portion 225) of the light receiving portion 225 by using a known technology, and it is possible to measure the bio-information, such as a photoelectric pulse wave, a volume pulse wave, a pulse rate (heart rate), a blood flow velocity, a blood flow rate, a blood perfusion amount, a vascular resistance, a blood pressure (a diastolic blood pressure and a systolic arterial pressure), or SpO2 (arterial oxygen saturation). The SpO2 can be acquired by using absorbance of oxyhemoglobin and reduced hemoglobin in each of the wavelengths, based on an output value of the light receiving portion 225 obtained by emitting the irradiation light having the first wavelength and the second wavelength in order from each of the light generating portions 221 and 223.

In addition, the heat flow sensor 21 or the optical sensor 22 may be disposed by allowing a part of the cover glass that covers the protective layer 213a of the heat flow sensor 21 and the optical sensor 22 to be projected from the rear surface of the main body case 10 so as to easily come into contact with the biological surface when the electronic device 1 is being installed. By improving the contact properties, deterioration of measurement accuracy is prevented.

The motion sensor 23 measures the motion of the user, and for example, can be realized by a 9-axis sensor which detects an acceleration (3-axis), an angular velocity (3-axis), and terrestrial magnetism (3-axis). By performing the arithmetic processing by using a known technology with respect to each of the output values, such as the acceleration, the angular velocity, and terrestrial magnetism of the motion sensor 23, it is possible to measure information, such as a quantity of physical activities, number of steps, a movement distance, a velocity, a posture (for example, "standing", "sitting", and "prone positions"), or the type of movement (behavior) (for example, "walking", "running", or "stepping the stairs") of the user.

The GPS sensor 24 is a sensor which detects a position or the like of the user by receiving a GPS satellite signal which is sent from a GPS satellite that is one type of a positioning satellite, and by using the received GPS satellite signal. In the embodiment, a residential area of the user is set from the detection result of the GPS sensor 24. In addition, since a method of detecting the position or the like of the user by using the GPS is known, a specific description thereof will be omitted.

Figure 6:
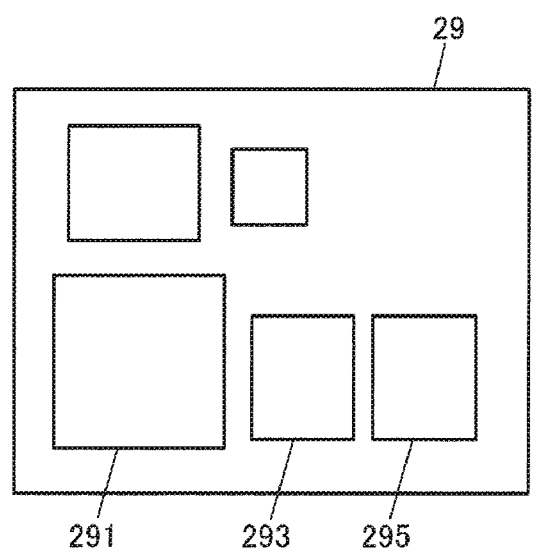
FIG. 6 is a plan view schematically illustrating a control substrate.

In addition, the electronic device 1 is provided with a control substrate 29 embedded in the main body case 10. The control substrate 29 is accommodated in a space on the rear surface side of the character plate 11. FIG. 6 is a plan view schematically illustrating the control substrate 29. On the control substrate 29, electronic components, such as a central processing unit (CPU) 291, a storage medium 293 (for example, an integrated circuit (IC) memory or a hard disk), and a wireless communication module 295, are loaded. In addition to this, necessary electronic components, such as an application specific integrated circuit (ASIC) or various types of integrated circuits, can be loaded, and an IC, a circuit or the like which drives and controls the sensors 21 to 24 are appropriately loaded. The electronic device 1 performs processing necessary for calculating the biological clock time, by executing a program stored in the storage medium 293 by the CPU 291.

Principles

In the embodiment, as an example of the bio-information which periodically varies in accordance with circadian rhythm (biorhythm on a daily basis: hereinafter, simply referred to as "biorhythm"), a deep body temperature (body temperature) of the part to be measured (in the embodiment, wrist) is illustrated as an example. The deep body temperature can be measured (calculated) by a relational expression based on a heat conduction equation, from the heat flow and the skin temperature of the biological surface which are obtained by the heat flow sensor 21. Measurement of the deep body temperature is consecutively performed.

Figure 7:
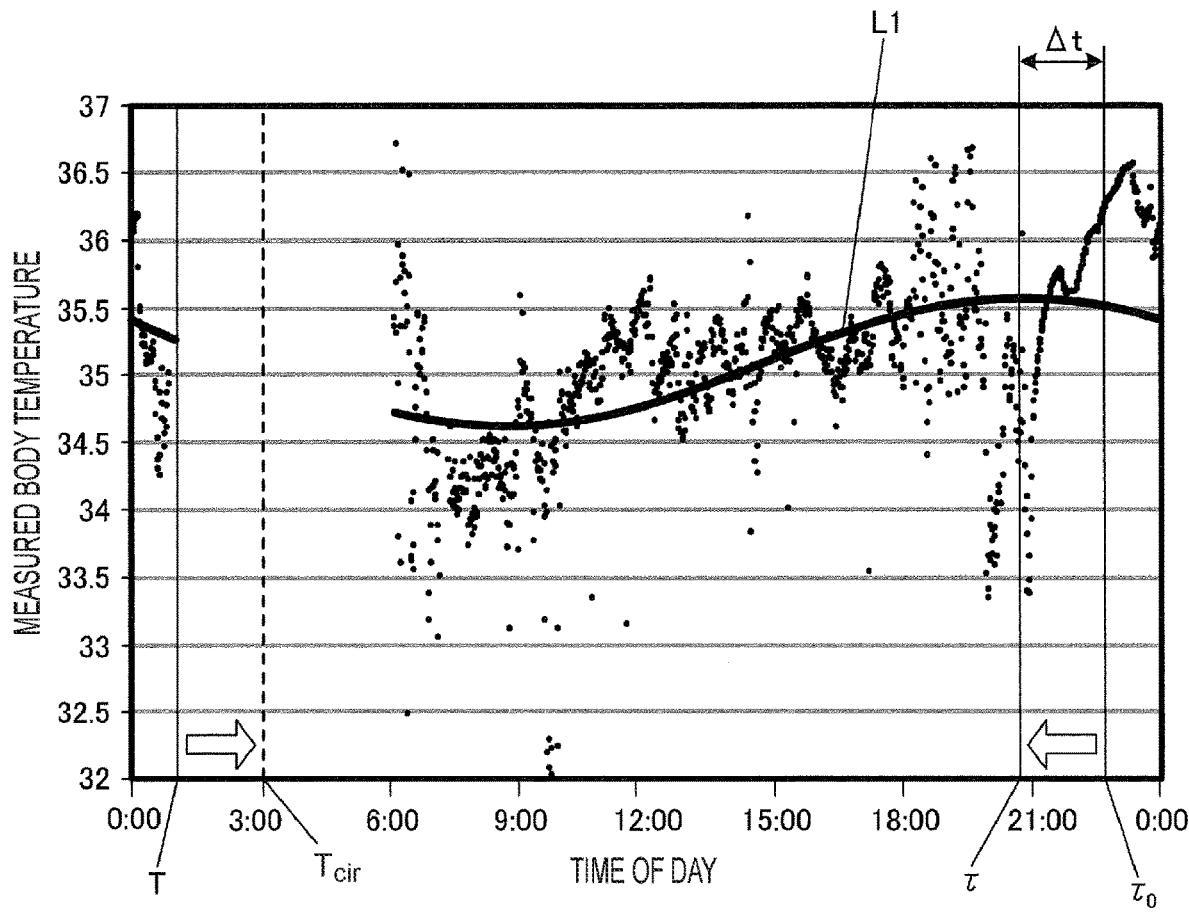
FIG. 7 is a view illustrating an example of a time transition of a measured deep body temperature.

FIG. 7 is a view illustrating a time transition of the measured deep body temperature, and illustrates the time transition by plotting a measured value obtained after the start of the measurement at 6:00 A.M. to the finish of the measurement at 1:00 A.M. of the next day. As illustrated in FIG. 7, the deep body temperature repeats periodic variation on a daily basis. Specifically, the deep body temperature increases from the morning to the afternoon, and becomes the highest in a time zone from the evening to the night. After this, the temperature decreases until the next morning.

1. Calculation of Biological Clock Time

Hereinafter, the calculation of the biological clock time will be described considering that the current time (practical time) is 1:00 A.M. at which the measurement of the deep body temperature is finished. First, the expression time of a characteristics period is calculated from a time series change of the measured deep body temperature. Therefore, first, a relational expression of a biorhythm curve L1 of one period (for example, 24 hours) of the deep body temperature which is close to a time change of the deep body temperature, is calculated from the measured value of the deep body temperature. In FIG. 7, the biorhythm curve L1 of one period which is calculated by using the measured value from 6:00 A.M. of a previous day to 1:00 A.M. which is the current time, is illustrated.

As a specific calculation method of the biorhythm curve L1, for example, it is possible to use a cosinor method. Here, it is assumed that the biorhythm is expressed by a trigonometric function in which 24 hours is one period, and fitting is performed with respect to the measured value according to a least squares method. A relational expression Y of the biorhythm curve L1 is expressed by the next equation (1). In the equation (1), M is an average value, A is an amplitude, ω is an angular frequency, t is time, and φ is an acrophase. In addition, the method is not limited to the method in which the cosinor method is used, and the fitting by using an additional periodic function may be performed.

$$Y = M + A \cdot \cos(\omega t - \phi) \quad (1)$$

Here, there is the acrophase in one characteristics period of the biorhythm. The time of the acrophase is called an acrophase time. In the embodiment, by calculating an expression time (time when the body temperature is the highest in one day: hereinafter, referred to as "characteristics period expression time") τ of the acrophase in the biorhythm curve L1 acquired from the measured value of the deep body temperature, the acrophase time is specified. In the example of FIG. 7, when converting the acrophase φ of the equation (1) to a time, the characteristics period expression time τ is 20:45 P.M. The conversion equation is illustrated in the next equation (2).

$$\tau = \phi \cdot \frac{24}{2\pi} \quad (2)$$

In addition, the characteristics period is not limited to the above-described acrophase. For example, a time having a large time change amount in the biorhythm curve of one period may be used as the characteristics period. Even in this case, a time differential value of the measured value, a difference value for each unit time or the like is acquired, and the time at which the value becomes the highest or the smallest is calculated as the characteristics period expression time.

In addition, a configuration of selecting the characteristics period which is appropriate in calculation of the biological clock time, from the plural characteristics periods, may be employed. The characteristics period which is appropriate in calculation is selected, for example, in accordance with the type of the bio-information to be measured, and in addition to this, can be selected in accordance with a use state or the like of the electronic device 1 by the user. In other words, a use state where the electronic device 1 is generally used during the day time and the electronic device 1 is removed from the user and the measurement is stopped during the night time, such as while the user sleeps, is also considered. Meanwhile, in a case of measuring the deep body temperature as the bio-information, the acrophase time is generally in a time zone of a night time, and thus, in the above-described use state, a situation in which the measured value of the characteristics period expression time is not obtained, is generated. In this case, the calculation accuracy of the biological clock time can be improved when using the characteristics period expression time calculated based on the time change amount in the time zone during the day time during which the measured value is obtained, rather than using the acrophase time.

When the characteristics period expression time $\tau$ is calculated, a time difference (hereinafter, referred to as "characteristics period time difference") $\Delta\tau$ between the characteristics period expression time $\tau$ and a reference expression time (hereinafter, referred to as "characteristics period reference expression time") $\tau_0$ of the acrophase, is calculated. The characteristics period time difference $\Delta\tau$ is expressed by the next equation (3).

$$\Delta\tau = \tau_0 - \tau \quad (3)$$

The characteristics period reference expression time $\tau_0$ is set in advance, for example, by measuring the deep body temperature considering a healthy person (sample person) as a target, and by collecting the characteristics period expression time. More specifically, the characteristics period reference expression time $\tau_0$ is used in each body profile section which divides the body profile, such as gender or age. In the embodiment, the gender is divided into male and female, and the age is divided by dividing the obtained values into stages. In addition, the characteristics period reference expression time $\tau_0$ is set for each of the body profile sections considering each of the above-described combinations of the sections related to each of the body profiles, as one body profile section (refer to a reference expression time table 372 of FIG. 9). In addition, in addition to the gender or the age, for example, the body profile section may be subdivided by further using the body profile, such as height or weight. In addition, the characteristics period reference expression time $\tau_0$ is set with respect to not only the wrist but also each measurement part that can be assumed.

In addition, when calculating the characteristics period time difference $\Delta\tau$, the characteristics period reference expression time $\tau_0$ which corresponds to the body profile and the measurement part (wrist) of the user is read out from the reference expression time table 372, and is used after being corrected based on the residential area of the user. This is because the characteristics period reference expression time $\tau_0$ varies according to the body profile or the measurement part, and varies according to the residential area.

For example, in a case of young and elderly people, it is known that the maximum value and the minimum value of the deep body temperature on a daily basis vary, and the time zone in which the characteristics period is expressed also changes in accordance with the age. The gender or the measurement part also similar. Here, when setting the characteristics period reference expression time $\tau_0$, the sample persons of which the body profile varies are gathered, the deep body temperature is measured for each measurement part, and the characteristics period expression time is collected from the biorhythm curve of one period. In addition, by classifying the collected characteristics period expression time by the body profile section which corresponds to the body profile of the corresponding sample person, and by acquiring, for example, an average value or a center value at each measurement part, each of the characteristics period reference expression times $\tau_0$ is obtained.

Meanwhile, the acrophase time varies receiving the influence of duration of sunshine. Specifically, the activity time becomes shorter and the sleeping time becomes longer as the duration of sunshine decreases. It is considered that this is because a secretion amount of melatonin depends on the duration of sunshine. The duration of sunshine can be specified from the residential area of the user and the season (for example, four seasons) in the residential area. The duration of sunshine is long in a plain area, and is short in a mountain area. In addition, this is also because the duration of sunshine is long in summer, and is short in winter. In addition, in the embodiment, in each area assumed as the residential area of the user, a corrected value of the characteristics period reference expression time $\tau_0$ according to each season is set in advance (refer to a reference expression time correction table 373 of FIG. 10). The corrected value is determined based on the duration of sunshine of the corresponding season in the corresponding area. According to this, even in a case where the user moves to the region having different duration of sunshine, it is possible to calculate the biological clock time with high accuracy.

When the characteristics period time difference $\Delta\tau$ according to the equation (3) is calculated, a biological clock time (circadian clock time) $T_{cir}$ is calculated from the calculated characteristics period time difference $\Delta\tau$ and the current time. For example, the characteristics period reference expression time $\tau_0$ is 22:45 P.M. In this case, in the example of FIG. 7, since the characteristics period expression time $\tau$ is 20:45 P.M., the current biological clock time of the user is advanced by two hours. Therefore, the biological clock time $T_{cir}$ advances by two hours from 1:00 A.M. of the current time T and is calculated as 3:00 A.M. of the day. In addition, although not being illustrated, in a case where the characteristics period expression time $\tau$ is 0:45 A.M., the current biological clock time of the user is delayed by two hours. In this case, the biological clock time $T_{cir}$ goes back by two hours from 1:00 A.M. of the current time T, and is calculated as 11:00 P.M. of the previous day. The biological clock time $T_{cir}$ is expressed by the next equation (4).

$$T_{cir} = T + \Delta\tau \quad (4)$$

2. Informing Processing

The electronic device 1 performs various types of informing based on the biological clock time. In addition to the informing performed with respect to the user (target person to be measured), the informing includes the informing with respect to a person other than the user, for example, the informing with respect to a health care provider or nursing staff in a case where the target person to be measured is a hospitalized patient or a person who requires nursing care, or the informing with respect to a protector in a case where the target person to be measured is a child.

(1) First Informing Processing

First informing processing is informing processing of informing the biological clock time and informing the time difference (that is, the characteristics period time difference $\Delta\tau$) between the biological clock time and the current time. In the embodiment, the display of the biological clock time by the second needle 114 on the character plate 11 is performed as the first informing processing. In other words, the first informing processing is realized by the needle handling control of the second needle 114. In addition, since the display of the current time by the first needle 111 on the character plate 11 is also performed, according to each of the time displays, the time difference between the biological clock time and the current time is also informed. Therefore, when seeing the character plate 11, the user can easily confirm the biological clock time or the time difference between the biological clock time and the current time, and instinctively grasp the current state of the biological clock.

In addition, in a case where each of the times is digital-displayed by using the display device, such as the touch panel, the time difference is displayed together with each of the time displays, and the first informing processing is performed. Otherwise, in accordance with an operation input of the user, any one of the display of the biological clock time and the display of the time difference may be displayed by switching the displays to each other.

(2) Second Informing Processing

Second informing processing is informing processing of performing the informing related to the biorhythm of the user, by using the biological clock time.

A well-regulated life according to the biorhythm is important in health management. For example, when paying attention to bathing or sleeping, bathing and urging heat radiation before and after the highest body temperature time (that is, the characteristics period expression time $\tau$) in one day which is the acrophase time, and going to bed after a while, is considered to be excellent. Here, in the embodiment, since the biological clock time is calculated considering the biological clock time (which matches the characteristics period reference expression time $\tau_0$, and in the example of FIG. 7, 22:45 P.M.) of the characteristics period expression time $\tau$, the deep body temperature becomes the highest at the time when the biological clock time is 22:45 P.M. Therefore, regarding the biorhythm of the user, it can be said that bathing and going to bed considering the practical time at which the biological clock time becomes 22:45 P.M. as a reference, is excellent. However, there are individual differences in the practical time at which the biological clock time becomes 22:45 P.M., and the biological clock time varies according to the user.

Here, in the embodiment, the biological clock time which is optimal for various activities of daily life, such as waking-up, eating, napping, bathing, or going to bed, is set as informing timing (second informing processing timing) in advance based on the biological clock time. In addition, at a point of time at which the biological clock time of the user becomes the second informing processing timing, an alert which indicates that the time is the biological clock time optimal for the corresponding activity of daily life, is notified.

A method of the informing may be a sound output of an informing sound from the speaker 14, or may be lighting or flickering the LED 15. At this time, at each of the second informing processing timings (that is, every type of the optimal operations of daily life at the timing), the informing sound, or the color of emitted light or the flickering pattern of the LED 15, may be changed. In addition, in a case where the electronic device 1 is provided with the display device, the electronic device 1 may be configured to display the alert. In addition to this, the informing may be performed by vibration by using a vibrator. In addition, a configuration in which a control signal for performing the notifying of the alert is sent to the external electronic device 5, and the above-described informing is performed by the external electronic device 5, can also be employed.

According to the second informing processing, it is possible to inform that the biological clock time which is appropriate for various activities of daily life that are generally performed from waking-up to bedtime is reached, with respect to the user according to the biological clock time of the user.

(3) Third Informing Processing

For example, the time when the characteristics period expression time $\tau$ is reached in a case where the biological clock time is delayed by six hours, becomes 4:45 A.M. of the next day after six hours after the characteristics period reference expression time $\tau_0$ (for example, 22:45 P.M.). As described above, the characteristics period expression time $\tau$ is the highest body temperature time of one day, and is the practical time which corresponds to the optimal biological clock time from the bathing to the bedtime for the user who uses the electronic device 1. Therefore, a large shift (disturbance of biorhythm) of the biological clock time, which is six hours described above, can be a reason that has a negative influence on a health state, for example, insufficiency of sleeping in which sleeping is not easy even when the user tries to sleep at about 22:45 P.M. which is the general bedtime, that is the characteristics period reference expression time $\tau_0$, is caused.

Here, it is determined whether or not the time difference (that is, the characteristics period time difference $\Delta\tau$) between the biological clock time and the current time satisfies the predetermined threshold value condition. In the embodiment, even when the threshold value condition is satisfied in a case where the characteristics period time difference $\Delta\tau$ is equal to or greater than the allowable shift time (for example, two hours) which is set in advance, the third informing processing is performed. The allowable shift time is set in advance by performing experimental study or the like based on a medical study. At this time, the allowable shift time may be set for each body profile section. Otherwise, the allowable shift time may be set by receiving the operation input of the user.

Examples of the informing contents include eating, bathing, waking-up, going to bed, turning-off of the light, necessity or stopping of exercise, intellectual activities, such as studying, and notifying of an alert to urging the taking or administrating of medicine. The method of the informing is similar to that of the second informing processing.

Otherwise, the display of an advice that suggests a recommendation value or the like regarding various items, such as menu or an amount of a meal, a bathing temperature or bathing time, rest time, bedtime, sleeping time, waking-up time, a quantity of illumination light, an environmental temperature, exercise contents or exercise time, contents or time of intellectual activities, viewing time of television, use time of electronic devices (for example, a personal computer or a smartphone), and the type or the amount of medicine to be taken or administered, can be an example.

As more specific contents of the advice, an advice, such as advising to have early bathing or light exercise, advising to have a meal containing capsaicin (for example, curry or red pepper cuisine), or advising to take biorhythm regulating medicine (benzodiazepine or the like), are considered. By carrying out these, it is possible to raise the body temperature, to urge heat radiation, and to improve the biorhythm.

The display of the advice is performed by the external electronic device 5 by sending the text data of the advice contents and the control signal for performing the display thereof to the external electronic devices 5. However, when the electronic device 1 is provided with the display device, the electronic device 1 may perform the display by itself. In addition, a configuration of outputting a sound by reading the text data of the advice contents may be employed.

Here, the third informing processing may be performed at the timing when the biological clock time is calculated, but in order to improve the biorhythm, it is more effective to perform the third informing processing at the timing when the practical time is considered. For example, regarding the meal, it is a status in which an alert is notified at the practical time (around noon in a case of lunch) at which the user generally has a meal, or an advice is displayed. Here, in the embodiment, the practical time at which various activities of daily life are generally performed is set in advance as the informing timing (third informing processing timing) based on the practical time. In addition, at the point of time when the current time becomes the third informing processing timing, an alert which indicates the practical time appropriate for the corresponding activity of daily life, is notified, or an advice is displayed.

In addition, regarding the third informing processing, the informing items may be set in accordance with the operation input of the user. For example, the informing may be performed with respect to "meal" and "exercise" among the items illustrated as examples of the informing contents, and the user may perform the setting operation in which the informing is not performed with respect to other items. According to this, the informing only with respect to the items that the user desire can be performed.

According to the third informing processing, it is possible to realize the notification of the alert that corresponds to the time difference between the biological clock time of the user and the current time or the display of the advice, and the user can apply the informing contents in improvement of the biorhythm.

3. Control of Home Electronic Appliances

The electronic device 1 performs an operation control of the home electronic appliance 7 based on the biological clock time.

(1) First External Device Control Processing

The first external device control processing is processing of sending a given control signal based on the biological clock time to the home electronic appliance 7. In the embodiment, at the home appliance control timing (first external device control processing timing) based on the biological clock time, the control signal for controlling the operation of the home electronic appliance 7 which corresponds to the corresponding activity of daily life is sent to the home electronic appliance 7. A relationship between the biological clock time and the activity of daily life is as described in the second informing processing.

For example, regarding the waking-up, it is known that the deep body temperature increases from the time before the waking-up to the time after the waking-up. Therefore, one specific example of operation control contents includes a control of setting the timing before and after the biological clock time related to the waking-up as the first external device control processing timing, inputting a power source of air conditioning equipment, and gradually raising the temperature setting. The electronic device 1 sends the control signal for this to the home electronic appliance (here, the air conditioning equipment) 7.

According to the first external device control processing, it is possible to realize the operation control of the home electronic appliance 7 based on the biological clock time of the user, and to provide a living environment appropriate for the state of the current biological clock.

(2) Second External Device Control Processing

The second external device control processing is performed in a case where the threshold value condition described in the third informing processing is satisfied. Specifically, at the home electronic appliance control timing (second external device control processing timing) based on the practical time, the control signal for controlling the operation of the home electronic appliance 7 which corresponds to the corresponding activity of daily life is sent to the corresponding home electronic appliance 7. The relationship between the practical time and the activity of daily life is as described in the third informing processing.

For example, it is known that the biological clock time is corrected when being exposed to sunlight in the morning. Therefore, one specific example of the operation control contents includes a control of setting the general waking-up time (practical time) as the second external device control processing timing, emitting the illumination light which is close to the sunlight by the illumination device, and opening an electric curtain (light controlling device). The electronic device 1 sends the control signal for this to the home electronic appliance (here, the illumination device or the light controlling device) 7.

In addition, the control signal is not limited to a configuration of being directly sent to the home electronic appliance 7, and may be configured to be sent to the home electronic appliance 7 via the external electronic device 5.

Functional Configuration

Figure 8:
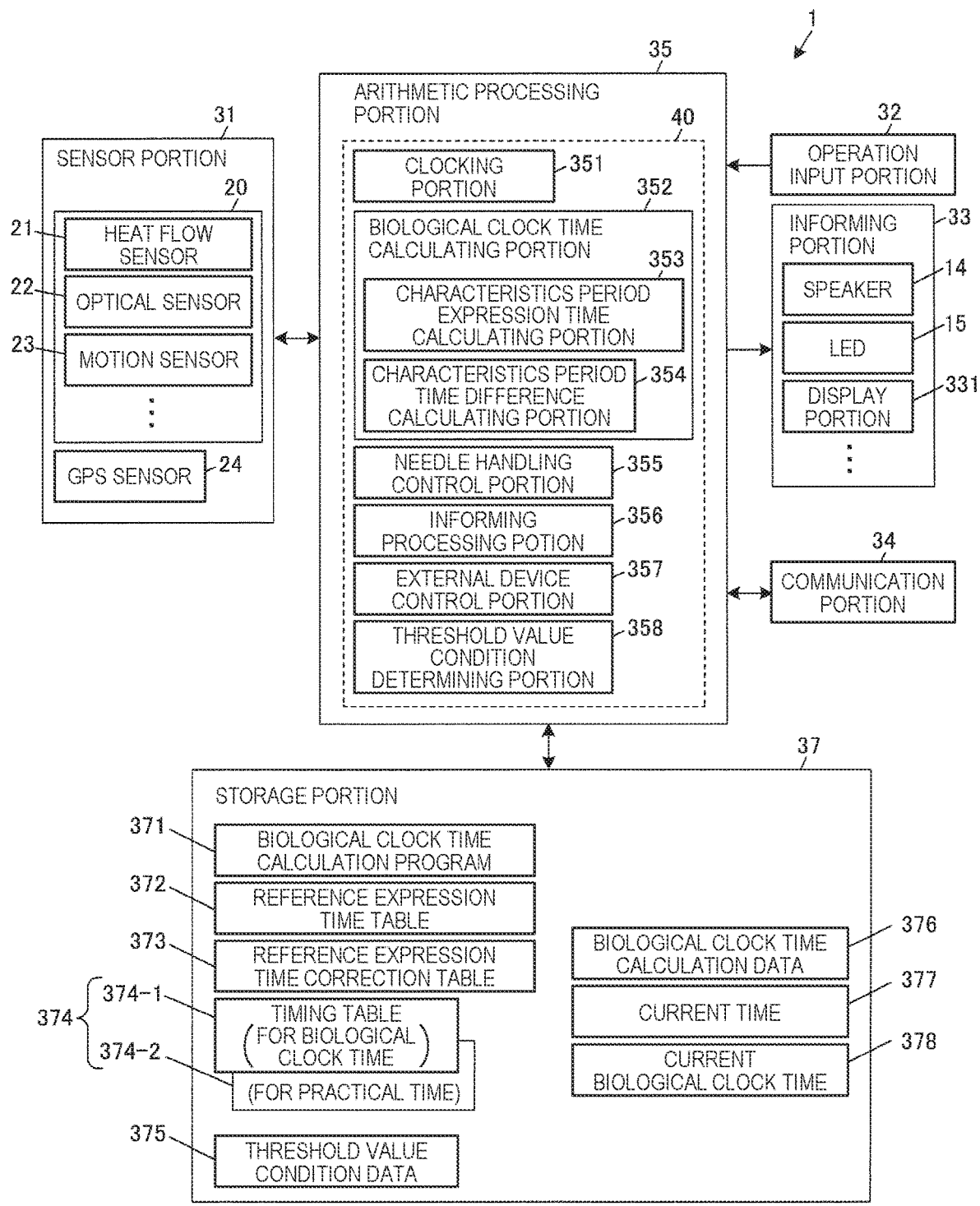
FIG. 8 is a block diagram illustrating a main functional configuration example of the electronic device.

FIG. 8 is a block diagram illustrating a main functional configuration example of the electronic device 1. As illustrated in FIG. 8, the electronic device 1 includes a sensor portion 31, an operation input portion 32, an informing portion 33, a communication portion 34, an arithmetic processing portion 35, and a storage portion 37.

The sensor portion 31 is configured of a plurality of sensors, such as the heat flow sensor 21 or the optical sensor 22, the motion sensor 23, and the GPS sensor 24 which are illustrated in FIG. 2 or 3. Among these, the heat flow sensor 21, the optical sensor 22, and the motion sensor 23 configure a measuring portion 20.

The operation input portion 32 receives various operation inputs by the user, and outputs the operation input signal which corresponds to the operation input to the arithmetic processing portion 35. It is possible to realize the operation input portion 32 by a button switch or a lever switch, a dial switch, or a touch switch. In FIG. 2, the operation switches 121 and 123 correspond to this.

The informing portion 33 is configured by appropriately including a display portion 331 in addition to the speaker 14 or the LED 15 which is illustrated in FIG. 2. The display portion 331 is realized by the display device, such as a liquid crystal display (LCD), an organic electroluminescence display (OELD), and an electronic paper display, and performs various displays based on the display signal from the arithmetic processing portion 35.

The communication portion 34 is a communication device for sending and receiving data to and from the outside under control of the arithmetic processing portion 35. As a communication method of the communication portion 34, various methods, such as a format of wireless connection by using the wireless communication, a format of wired connection via a cable that is based on a predetermined communication standard, or a format of connection via an intermediate device which is also used as a charger that is called a cradle or the like can be applied. In FIGS. 2 and 6, the wireless communication module 295 loaded on the control substrate 29 corresponds to this.

The arithmetic processing portion 35 performs input and output controls of the data between each of the functional portions, executes various types of arithmetic processing based on a predetermined program or data, an operation input signal from the operation input portion 32, and the measurement result of the sensors 21 to 24 which configure the sensor portion 31, and obtains the bio-information of the user. For example, the processing is realized by a microprocessor, such as a CPU or a graphics processing unit (GPU), or an electronic component, such as an ASIC or an IC memory. In FIGS. 2 and 6, the CPU 291 loaded on the control substrate 29 corresponds to this.

The arithmetic processing portion 35 includes a clocking portion 351, a biological clock time calculating portion 352, a needle handling control portion 355, an informing processing potion 356, an external device control portion 357, and a threshold value condition determining portion 358.

The clocking portion 351 clocks a current time 377 by using a system clock.

The biological clock time calculating portion 352 calculates the biological clock time $T_{cir}$ at the calculation timing of the biological clock time which is appropriately set, and rewrites a current biological clock time 378. In addition, after the biological clock time $T_{cir}$ is calculated until reaching the next calculation timing, the biological clock time is clocked by adding the latest characteristics period time difference $\Delta\tau$ to the current time 377, and the current biological clock time 378 is updated whenever necessary.

The biological clock time calculating portion 352 includes a characteristics period expression time calculating portion 353 and a characteristics period time difference calculating portion 354. The characteristics period expression time calculating portion 353 calculates a biorhythm curve for one period from measured value of the deep body temperature that varies on a daily basis, and calculates the expression time of the acrophase which is one example of the characteristics period as the characteristics period expression time $\tau$. The characteristics period time difference calculating portion 354 calculates the time difference between the characteristics period expression time $\tau$ and the characteristics period reference expression time $\tau_0$ as the characteristics period time difference $\Delta\tau$.

The needle handling control portion 355 controls the movement that drives and handles the first needle 111 and the second needle 114, and performs the needle handling control of the needles 111 and 114.

The informing processing potion 356 performs the informing based on the corresponding informing contents (second informing processing) at the informing timing (second informing processing timing) based on the biological clock time set in a timing table for the biological clock time 374-1, in accordance with the current biological clock time 378. In addition, the informing processing potion 356 performs the informing based on the corresponding informing contents (third informing processing) at the informing timing (third informing processing timing) based on the practical time set in a timing table for the practical time 374-2, in accordance with the current time 377.

The external device control portion 357 controls the operation of the corresponding home electronic appliance 7 (first external device control processing) by sending the corresponding control signal at the home electronic appliance control timing (first external device control processing timing) based on the biological clock time set in the timing table for the biological clock time 374-1, in accordance with the current biological clock time 378. In addition, the external device control portion 357 controls the operation of the corresponding home electronic appliance 7 (second external device control processing) by sending the corresponding control signal at the home electronic appliance control timing (second external device control processing timing) based on the practical time set in the timing table for the practical time 374-2, in accordance with the current time 377.

The threshold value condition determining portion 358 performs determination of the threshold value condition at the informing and home electronic appliance control timing based on the practical time.

The storage portion 37 is realized by the storage medium, such as an IC memory, a hard disk, or an optical disk. In the storage portion 37, a program for operating the electronic device 1 and realizing various functions of the electronic device 1, data to be used in executing the program, or the like is stored in advance, or is temporarily stored every time when the processing is performed. In FIGS. 2 and 6, the storage medium 293 loaded on the control substrate 29 corresponds to this.

In addition, in the storage portion 37, a biological clock time calculation program 371, the reference expression time table 372, the reference expression time correction table 373, the timing tables for the biological clock time and for the practical time 374-1 and 374-2 which function as a timing table 374, threshold value condition data 375, biological clock time calculation data 376, the current time 377, and the current biological clock time 378, are stored.

The arithmetic processing portion 35 realizes functions of the clocking portion 351, the biological clock time calculating portion 352, the needle handling control portion 355, the informing processing potion 356, the external device control portion 357, the threshold value condition determining portion 358, and the like by reading out and executing the biological clock time calculation program 371. In addition, in a case where the functional portions are realized by hardware, such as an electronic circuit, it is possible to omit a part of the program for realizing the function.

The reference expression time table 372 stores the characteristics period reference expression time $\tau_0$. FIG. 9 is a view illustrating a data configuration example of the reference expression time table 372. As illustrated in FIG. 9, in the reference expression time table 372, in association with the combination of each section of gender and age, the characteristics period reference expression time $\tau_0$ of the corresponding body profile section is set for each measurement part.

The reference expression time correction table 373 stores the corrected value of the characteristics period reference expression time $\tau_0$. FIG. 10 is a view illustrating a data configuration example of the reference expression time correction table 373. As illustrated in FIG. 10, in the reference expression time correction table 373, in association with area information which determines one residential area, the duration of sunshine of the residential area, and the corrected value of the characteristics period reference expression time $\tau_0$ employed in the user of the residential area, are set for each season. The area information includes the name of the country, the name of the region, such as the name of the state or city, and positional information, such as latitude and longitude.

The timing table for the biological clock time 374-1 stores the relationship between the biological clock time and the activities of daily life. In addition, the timing table for the practical time 374-2 stores the relationship between the practical time and the activities of daily life. FIG. 11 is a view illustrating a data configuration example of the timing table for the biological clock time 374-1. As illustrated in FIG. 11, in the timing table 374-1, in association with various types of activities of daily life, the informing and home electronic appliance control timing based on the biological clock time which is considered as the second informing processing timing or the first external device control processing timing, the informing contents, such as the notifying contents of an alert which is generated at the corresponding timing, and the control signal of the home electronic appliance 7 which is sent at the corresponding timing, are set. In addition, although not illustrated, the timing table for the practical time 374-2 can be realized by the data configuration similar to the timing table 374-1. In other words, in association with various types of activities of daily life, the informing and home electronic appliance control timing based on the practical time which is considered as the third informing processing timing or the second external device control processing timing, the informing contents, such as the notifying contents of an alert which is generated at the corresponding timing or the display contents of an advice, and the control signal of the home electronic appliance 7 which is sent at the corresponding timing, are set.

The threshold value condition data 375 stores the allowable shift time for each body profile section.

The biological clock time calculation data 376 stores the relational expression of the biorhythm curve obtained in the process of calculating the biological clock time $T_{cir}$, or each value of the characteristics period expression time $\tau$, the characteristics period reference expression time $\tau_0$, the characteristics period time difference $\Delta\tau$, and the biological clock time $T_{cir}$, as history.

Flow of Processing

Figure 12:
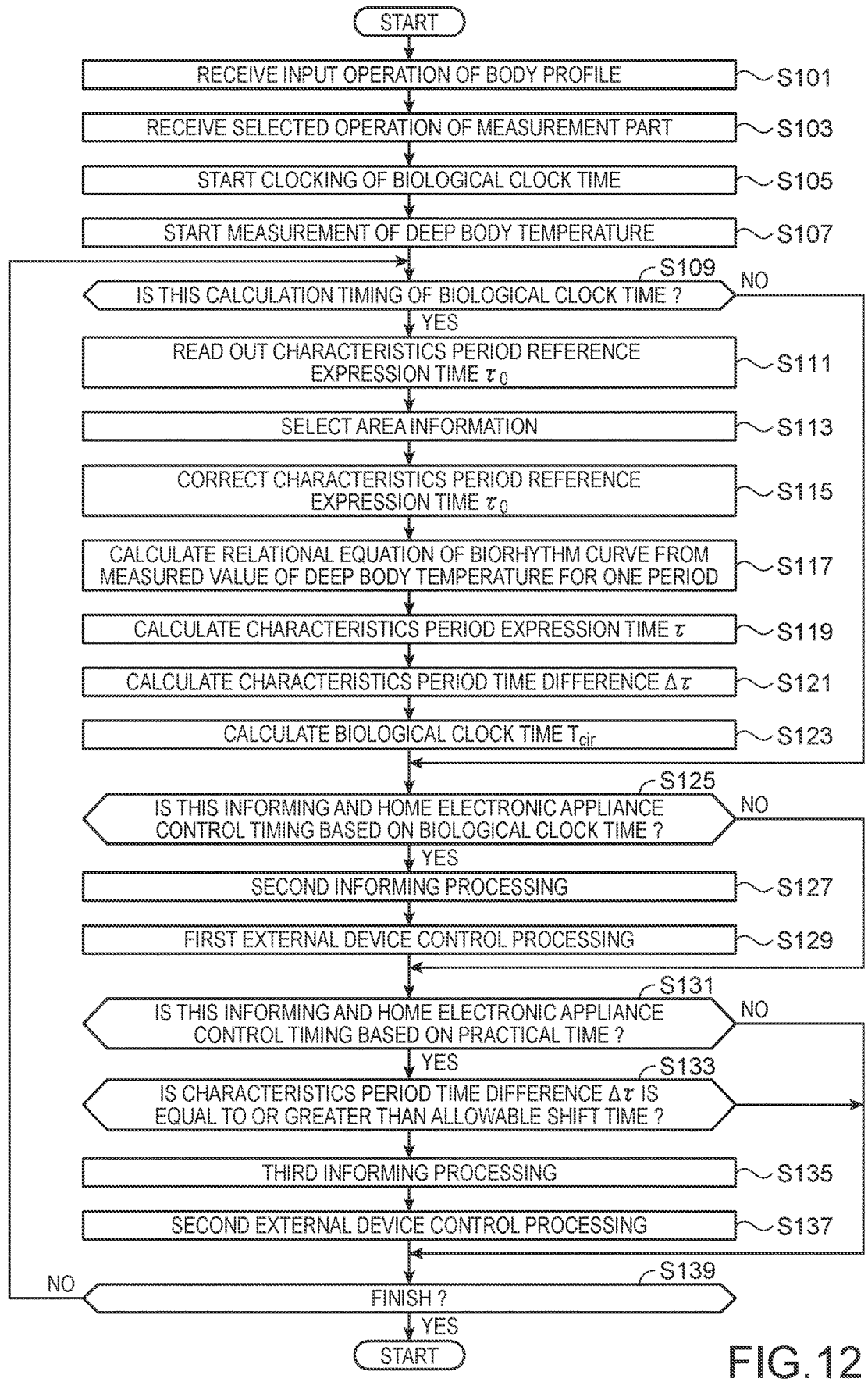
FIG. 12 is a flowchart illustrating a flow of processing performed by the electronic device.

FIG. 12 is a flowchart illustrating a flow of processing performed by the electronic device 1. The processing described here can be realized by reading out and executing the biological clock time calculation program 371 from the storage portion 37 by the arithmetic processing portion 35, and by operating each portion of the electronic device 1. Before starting the processing, the electronic device 1 is installed on the user.

First, the arithmetic processing portion 35 receives the input operation of each of the body profiles, such as gender or age, via the operation input portion 32 (step S101) and receives the selected operation by presenting a list of the parts to be measured set in the reference expression time table 372 (Step S103). The user inputs own values of each of the body profiles, and selects the measurement part at which the electronic device 1 is installed.

After this, the biological clock time calculating portion 352 starts the clocking of the biological clock time (step S105). In addition, the clocking of the biological clock time is performed by using the latest characteristics period time difference $\Delta\tau$ obtained in the process during the previous biological clock time calculation. Therefore, when executing the processing for the first time, after waiting for the calculation of the characteristics period time difference $\Delta\tau$ in step S121 of the later stage, the clocking of the biological clock time is started.

After this, the measurement of the deep body temperature is started (Step S107).

When starting the measurement of the deep body temperature, the biological clock time calculating portion 352 monitors the calculation timing of the biological clock time set in advance in accordance with the current time 377. The calculation timing may be set to be fixed, for example, performing the calculation at 0:00 A.M., or may be set by receiving the operation input of the user. Otherwise, a configuration in which the processing after step S111 is performed in a case where there is an indication operation which indicates the calculation of the biological clock time by the user may be employed.

In addition, in a case of the calculation timing (step S109: YES), the biological clock time calculating portion 352 refers to the reference expression time table 372, specifies the body profile section of the user, and reads out the characteristics period reference expression time $\tau_0$ which corresponds to the measurement part (step S111). Next, the biological clock time calculating portion 352 refers to the reference expression time correction table 373, and selects the area information in which the user is positioned based on the detection result of the GPS sensor 24 (step S113). In addition, the biological clock time calculating portion 352 specifies the season based on the current time 377, and corrects the characteristics period reference expression time $\tau_0$ read out in step S111 by using the corrected value of the specified season that corresponds to the selected area information (step S115).

Next, the characteristics period expression time calculating portion 353 calculates the relational expression of the biorhythm curve from the measured value of the deep body temperature for one period going back from the current time 377 (step S117), and calculates the characteristics period expression time $\tau$ (step S119). In addition, the characteristics period time difference calculating portion 354 calculates the characteristics period time difference $\Delta\tau$ which is a time difference between the characteristics period expression time $\tau$ and the characteristics period reference expression time $\tau_0$ corrected in step S115 (step S121). After this, the biological clock time calculating portion 352 calculates the biological clock time $T_{cir}$ by adding the characteristics period time difference $\Delta\tau$ to the current time 377 (step S123). At this time, the current biological clock time 378 is rewritten in accordance with the calculated biological clock time $T_{cir}$.

In addition, the arithmetic processing portion 35 monitors the current biological clock time 378, and determines the informing and home electronic appliance control timing based on the biological clock time set in the timing table for the biological clock time 374-1. In addition, at the corresponding timing (step S125: YES), the informing processing potion 356 performs the informing based on the corresponding informing contents by performing the second informing processing (step S127). In addition, the external device control portion 357 performs the first external device control processing, and sends the corresponding control signal to the corresponding home electronic appliance 7 (step S129).

In addition, the arithmetic processing portion 35 monitors the current time 377, and determines the informing and home electronic appliance control timing based on the practical time set in the timing table for the practical time 374-2. In addition, at the corresponding timing (step S131: YES), the threshold value condition determining portion 358 reads out and uses the allowable shift time that corresponds to the body profile section of the user from the threshold value condition data 375, and determines the characteristics period time difference $\Delta\tau$ as a threshold value. In addition, in a case where the threshold value condition in which the characteristics period time difference Δτ is equal to or greater than the allowable shift time is satisfied (step S133: YES), the informing processing potion 356 performs the third informing processing, and performs the informing based on the corresponding informing contents (step S135). In addition, the external device control portion 357 performs the second external device control processing, and sends the corresponding control signal to the corresponding home electronic appliance 7 (step S137).

After this, until finishing the processing (step S139: NO), returning to step S109, the above-described processing is repeated.

As described above, according to the embodiment, it is possible to calculate the biological clock time by measuring and using the deep body temperature which changes on a daily basis. The user can grasp the time of the biological clock in which the biorhythm is made, and can apply the biological clock time in health management or the like.

Modification Example

In the above-described embodiment, the biological clock time is calculated by measuring and using the deep body temperature, but not being limited to the deep body temperature, other pieces of bio-information that changes on a daily basis may be used. Examples thereof include a pulse rate, a blood pressure, SpO2, a skin heat flow, and a blood flow amount.

Figure 13:
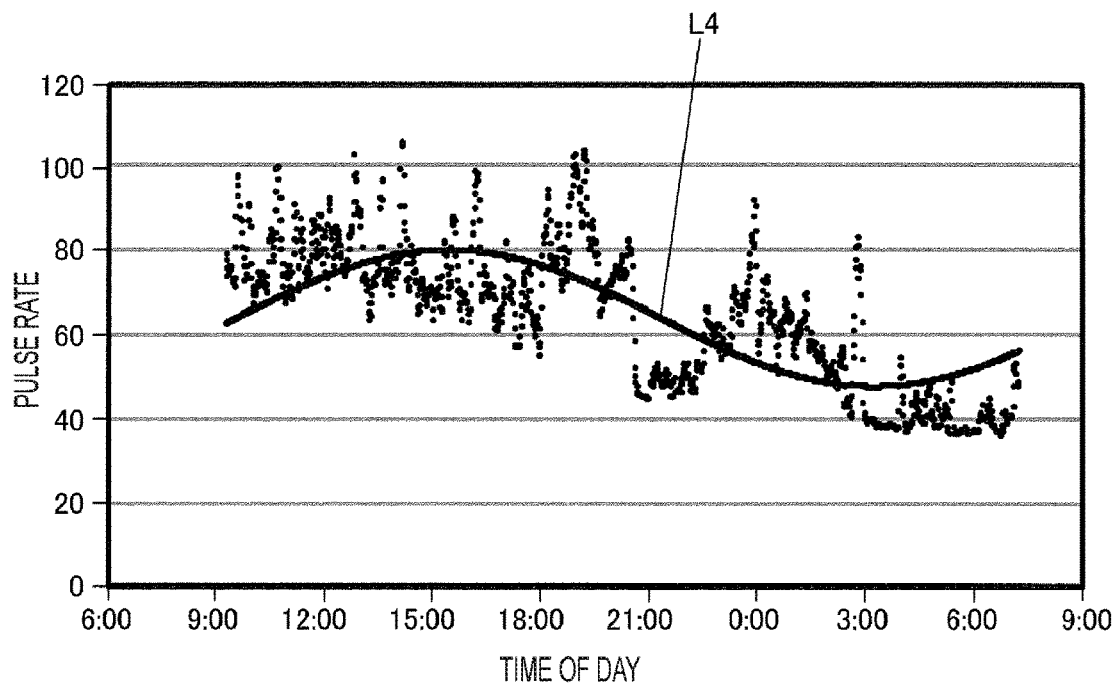
FIG. 13 is a view illustrating an example of the time transition of a pulse rate.

FIG. 13 is a view illustrating an example of the time transition of the pulse rate, and illustrates the example combining with a biorhythm curve L4 obtained by fitting the measured value. Similarly, FIG. 14 is a view illustrating an example of a time transition of a diastolic blood pressure and a systolic arterial pressure, and illustrates the example combining a biorhythm curve L51 obtained by fitting the measured value of the diastolic blood pressure and a biorhythm curve L53 obtained by fitting the measured value of the systolic arterial pressure, respectively by a broken line and a solid line.

Figure 14:
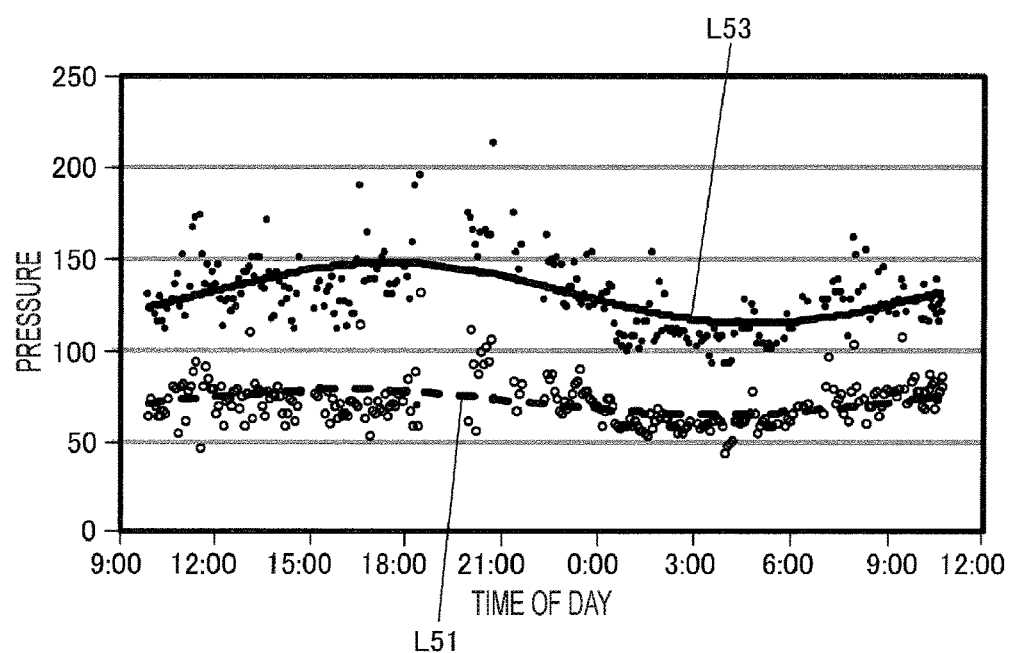
FIG. 14 is a view illustrating an example of a time transition of a diastolic blood pressure and a systolic arterial pressure.

When comparing the biorhythm curve of FIG. 13 or 14 or the biorhythm curve of FIG. 7, the characteristics period expression time (acrophase time) varies according to the bio-information, but any piece of bio-information also repeats the periodic change on a daily basis. Therefore, when the characteristics period reference expression time is set in advance with respect to the bio-information to be measured, it is possible to calculate the biological clock time in order similar to that of the above-described embodiment.

In addition, not being limited to the configuration of calculating the biological clock time by using one piece of bio-information, the biological clock time may be calculated for each bio-information by using the plural pieces of bio-information, and each of the calculated biological clock times may be displayed. According to this, the user can compare and confirm the biological clock time for each bio-information, and can grasp the entire balance of own biorhythm. For example, in a case of analog display, various needle handling controls may be performed by preparing the needles for each piece of bio-information. Meanwhile, in a case of digital display, the display target may be switched in accordance with the operation input of the user, and any one of the calculated biological clock times for each piece of bio-information may be selectively displayed. The biological clock time related to the blood pressure may average and display the biological clock time calculated from the systolic arterial pressure and the biological clock time calculated from the diastolic blood pressure.

In addition, the biological clock time related to the plural pieces of bio-information may calculate and display an average value. However, even in this case, it is appropriate to individually display the biological clock time related to the blood pressure. This is because there is a case where the characteristics period expression time of the blood pressure (for example, the time at which the blood pressure becomes the highest in one day) varies according to the season. Meanwhile, the characteristics period expression time, such as the deep body temperature or the pulse rate, is relatively stable, and does not largely vary through one year. Therefore, it is appropriate to display the average value of the biological clock time related to the deep body temperature or the pulse rate, and to display the biological clock time related to the blood pressure separately from the average value.

However, not being limited to the average value, the most frequent value of the biological clock time may be displayed by generating histogram of the calculated biological clock time for each piece of bio-information. In addition, pre-processing of excluding an abnormal value before acquiring the average value or the most frequent value, may be performed. In detecting the abnormal value, it is possible to use a method based on the statistics, a method by clustering, a method based on a density, and a method based on a distance. For example, a k-means method can be used.

In addition, the biological clock time may be calculated by estimating and using specific bio-information from the measurement result of the plural pieces of bio-information. The estimation is performed, for example, by obtaining a value of the specific bio-information from the measurement result of the plural types of bio-information by using a known mechanical learning technology. Examples of the specific bio-information include a melatonin concentration in the urine, a rectal temperature, and a tympanic temperature. Since the biorhythm appeared in these pieces of bio-information is relatively unlikely to receive the influence of disturbance, it is possible to calculate the characteristics period, such as the characteristics period expression time (acrophase time), with high accuracy, and to improve the calculation accuracy of the biological clock time. In addition, examples of the mechanical learning technology include a decision tree method, a random forest method, a neural network, and logistic regression.

In addition, one or plural pieces of bio-information may be measured at different measurement parts, and the biological clock time may be calculated and displayed for each measurement part. For example, by preparing the measuring device provided with the measuring portion 20 separately from the electronic device 1, the measuring device is installed at the measurement part other than the wrist. In this case, the electronic device 1 obtains the measurement result by performing the data communication between the measuring devices, or the like.

For example, when the measuring device is installed on the chest and measures the deep body temperature thereof, it is possible to calculate the biological clock time related to the temperature of a core part (core temperature). The biological clock of the core temperature is a main clock of a living body, and the biological clock of the deep body temperature measured at the wrist is considered as a peripheral clock. Therefore, by displaying both of the biological clock times, the user can grasp more detailed biorhythm.

In addition, in the above-described embodiment, the electronic device 1 is illustrated as the biological clock time calculating apparatus. Meanwhile, the biological clock time calculating apparatus can be configured as a biological clock time calculating module 40 which realizes the functions of each of the clocking portions 351 to 357 surrounded by the broken line in FIG. 8. In this case, the biological clock time calculating module 40 which is the biological clock time calculating apparatus calculates the biological clock time by inputting and using the measurement result of the measuring portion 20. According to this, by loading the biological clock time calculating module 40 on the control substrate 29, the function can be simply installed.

In addition, the biological clock time calculating apparatus may be configured excluding the measuring portion 20 in FIG. 8. For example, the heat flow sensor 21 or the optical sensor 22 is provided, and the measuring device (measuring portion) which is a separated body installed on the biological surface of the user is prepared. In addition, the biological clock time calculating apparatus may calculate the biological clock time by obtaining the measurement result by the data communication with the measuring device. The biological clock time calculating apparatus in this case can use the smartphone exemplified as the external electronic device 5, and the like in addition to a dedicated device.

In addition, in accordance with the operation input of the user, or automatically, the calculation frequency of the biological clock time may be configured to be switched. For example, a consecutive measurement mode in which the calculation timing of the embodiment is short and the biological clock time is consecutively calculated, an instantaneous value measurement mode in which the biological clock time is singly calculated, and a non-measurement mode in which the calculation of the biological clock time is not performed, may be switched to each other. According to this, it is possible to perform the calculation of the biological clock time as necessary, and to reduce the charging frequency by suppressing the power consumption.

In addition, from the viewpoint of protecting privacy, a configuration of switching the display and non-display of the biological clock time in accordance with the operation input of the user, may be employed.

The entire disclosure of Japanese Patent Application No. 2016-155842 is hereby incorporated herein by reference.

What is claimed is:

1. An electronic device configured to be secured to a measurement part of a user, the electronic device comprising:
   at least one sensor configured to measure bio-information of the user that changes on a daily basis;
   an arithmetic processing portion that, based on a measurement result of the at least one sensor, calculates biological clock time by:
      setting a characteristics period reference expression time of the bio-information, the characteristics period reference expression time being obtained in advance based on measurements of bio-information of persons other than the user and being determined based on a body profile of the user and the measurement part to which the electronic device is to be secured;
      comparing the characteristics period reference expression time to a characteristics period expression time, which is obtained from the measured bio-information of the user during a preceding period of time; and
      adjusting a current time by a difference between the characteristics period reference expression time and the characteristics period expression time to yield the biological clock time; and
   an output portion that outputs the calculated biological clock time to the user.

2. An electronic device configured to be secured to a measurement part of a user, the electronic device comprising
   an input portion which inputs a measurement result of at least one sensor configured to measure bio-information of the user that changes on a daily basis;
   an arithmetic processing portion that, based on the input measurement result of the at least one sensor, calculates biological clock time by:
      setting a characteristics period reference expression time of the bio-information, the characteristics period reference expression time being obtained in advance based on measurements of bio-information of persons other than the user and being determined based on a body profile of the user and the measurement part to which the electronic device is to be secured;
      comparing the characteristics period reference expression time to a characteristics period expression time, which is obtained from the measured bio-information of the user during a preceding period of time; and
      adjusting a current time by a difference between the characteristics period reference expression time and the characteristics period expression time to yield the biological clock time; and
   an output portion that outputs the calculated biological clock time to the user.

3. The electronic device according to claim 2, wherein the arithmetic processing portion sets the characteristics period reference expression time also based on any of a residential area of the user and a season in the residential area.

4. The electronic device according to claim 1, wherein the output portion also outputs a time difference between the biological clock time and the current time.

5. The electronic device according to claim 1, wherein the output portion outputs information related to a biorhythm of the user by using the biological clock time.

6. The electronic device according to claim 1, wherein the arithmetic processing portion sends a given control signal based on the biological clock time to any of a home electronic appliance and an external electronic device.

7. The electronic device according to claim 1, wherein the arithmetic processing portion sends a given control signal to any of a home electronic appliance and an external electronic device in a case where the difference between the biological clock time and the current time satisfies a predetermined threshold value condition.

8. The electronic device according to claim 1, wherein the bio-information includes any one of a body temperature, a blood pressure, arterial oxygen saturation, and a pulse rate.

9. The electronic device according to claim 1, wherein the at least one sensor is configured to measure plural types of the bio-information, and
wherein the arithmetic processing portion estimates specific bio-information from a result of measuring the plural types of the bio-information, and calculates the biological clock time based on the specific bio-information.

10. The electronic device according to claim 1, wherein the output portion comprises:
   a first needle which indicates the current time;

a second needle which indicates the biological clock time; and a needle handling control portion which controls the first needle and the second needle.

11. A biological clock time calculating method comprising:

measuring, with at least one sensor of an electronic device configured to be secured to a measurement part of a user, bio-information of the user that changes on a daily basis;

calculating biological clock time based on a measurement result of the at least one sensor by:

setting a characteristics period reference expression time of the bio-information, the characteristics period reference expression time being obtained in advance based on measurements of bio-information of persons other than the user and being determined based on a body profile of the user and the measurement part to which the electronic device is to be secured;

comparing the characteristics period reference expression time to a characteristics period expression time, which is obtained from the measured bio-information of the user during a preceding period of time; and adjusting a current time by a difference between the characteristics period reference expression time and the characteristics period expression time to yield the biological clock time; and outputting the calculated biological clock time to the user.

* * * * *